United States Patent [19]
Furuya et al.

[11] Patent Number: 5,391,849
[45] Date of Patent: Feb. 21, 1995

[54] ELECTRICAL DISPOSAL APPARATUS OF USED INJECTION SYRINGE

[76] Inventors: Kenichi Furuya, 4-14-28, Eda-higashi, Midori-ku, Yokohama-shi, Kanagawa-ken; Tuyosi Matuno, 9-5, Mominokidai, Midori-ku, Yokohama-shi, Kanagawa-ken, both of Japan

[21] Appl. No.: 165,073

[22] Filed: Dec. 10, 1993

[30] Foreign Application Priority Data

May 14, 1993 [JP] Japan .............................. 5-030496[U]

[51] Int. Cl.6 .............................................. B23K 11/22
[52] U.S. Cl. ................................................... 219/68
[58] Field of Search ........................ 219/68; 110/250; 604/110

[56] References Cited

U.S. PATENT DOCUMENTS

| | | | |
|---|---|---|---|
| 4,628,169 | 12/1986 | Ching-Lung | 219/68 |
| 4,877,934 | 10/1989 | Spinello | 219/68 |
| 4,965,426 | 10/1990 | Colombo | 219/68 |
| 5,138,124 | 8/1992 | Kirk et al. | 219/68 |
| 5,245,935 | 9/1993 | Fukuda | 219/68 |
| 5,282,428 | 2/1994 | Greville et al. | 219/68 |
| 5,300,752 | 4/1994 | Elmerick et al. | 219/68 |

FOREIGN PATENT DOCUMENTS 2-68116  3/1990  Japan .

Primary Examiner—Geoffrey S. Evans
Attorney, Agent, or Firm—Koda and Androlia

[57] ABSTRACT

A disposal or waste apparatus for used or waste injection syringes including a housing with a power transformer, a fan, a deodorant cartridge and a scrap containing box, and a cartridge type electrode plate unit detachably provided to the housing. Cartridge type electrode plate unit has two insertion holes for injection syringes, and two pairs of electrodes separated from each other and cross each other in order to electrically contact with contact terminals of the electrode plates in the housing. The used syringes inserted through the insertion holes respectively come into contact with one pair of electrodes and melt by short circuit current flown between the electrodes and turn on the fan so that any odor gas generated is blown through the deodorant cartridge. The apparatus further includes a switch rod actuated by sliding of said scrap containing box to open a primary winding of said power transformer.

6 Claims, 10 Drawing Sheets

ELECTRICAL DISPOSAL APPARATUS OF USED INJECTION SYRINGE

BACKGROUND OF THE INVENTION

The present invention relates to a disposal apparatus for melting waste injection syringes or needles used in medical organizations such as hospitals.

Nowadays, in order to save hand works such as biling and sterlizing and make sure of safety on disinfection and the like, disposable injection syringes are widely employed in the medical organizations.

If the disposable injection syringes attached to the injection bodies are wasted, they may hurt medical people such as stinging people's fingers and hands while these injection syringes are detached from the injector bodies or put into a rubber bag and the like and conveyed to a waste depot or yard, resulting in heavy accidents such as infections of aids virus and virus hepatitis and the like.

In order to solve such problems, the conventional apparatus has been used which has a pair of electrodes separated from each other and contained in a housing of the apparatus, and waste injection syringes are inserted through injection syringe insertion holes and contact with the electrodes resulting in melting of the syringes by flash short-current between the electrodes.

According to the conventional apparatus, the electrodes are installed and secured in the housing, so that it is necessary to detach the electrodes and change them with new ones in narrow space of the housing when the electrodes fail to have good conductivity after they have been used for a long period causing worn-away or damage, or after they are melted and attached to the electrode surfaces. Further, according to the conventional apparatus, the distance between the electrodes separated from each other and fixed in the housing is previously determined. Consequently, it is necessary to use different apparatus when injection syringes of different size, for example thick syringes No. 18 (diameter: 1.8 mm) through No. 14 (diameter: 2.1 mm), are melted and disposed in the disposal apparatus or syringer destroyer. It is impossible to adopt only one apparatus treating waste syringes and destroying them. It has been a problem in the medical field.

The present invention has been accomplished after considering such problem and studying the present situation of the field.

SUMMARY OF THE INVENTION

Accordingly, major object of the present invention is to provide a disposal apparatus for used or waste injection syringes which apparatus makes electrodes-exchanges being necessitated after the electrodes are worn away or polluted simple and easy, and speedy of its operation by making the electrode plate unit provided with the electrodes a cartridge type structural one.

Another object of the present invention is to provide a disposal apparatus for used or waste injection syringes enabling to melt and dispose thin injection syringes (No. 30 to No. 21, diameter: 0.3 mm to 0.85 mm) of insertion type and thick injection syringes (No. 18 to No. 14, diameter: 1.8 mm to 2.1 mm) of screwed-in type by using the same electrode plate unit or without exchanging them with other and different electrode plate unit.

Still another object of the present invention is to provide a disposal apparatus for used or waste injection syringes enabling to melt and dispose them sanitarily, safely and without unpleasantness feelings of the operators after odor is deodorized and exhaled from the housing of the disposal apparatus.

According to the disposal apparatus for used or waste injection syringes of the present invention solving the problems of the conventional apparatus, the disposal apparatus has a housing provided with a power source transformer and a drawable scraps containing box or scrap box, and a cartridge type electrode plate unit detachable on the housing of the apparatus, the housing contains a deodorizer or deodrant filling portion in which deodorizer is packed and a fan for compulsorily exhausting odor gas generated while the waste injection syringes are melting and disposing to out of the housing, and a pair of electrode plate contact terminals connected to the secondary windings of the power transformer, and the cartridge type electrode plate unit has two injection syringe insertion holes and pairs of electrodes respectively crossed and separated from each other in order to melt and dispose thin and thick injection syringes inserted through these injection syringe insertion holes, wherein the distance between one of the electrodes and a guide electrode is kept at a fixed one correspondingly to the thickness of respective injection syringes, and the electrodes are arranged so as to electrically contact with the pair of electrode plate contacting terminals in the housing.

The foregoing object, other objects and advantages of the present invention will be made apparent from the following description described in reference to the accompanying drawings.

DETAILED DESCRIPTION OF THE INVENTION

Figure 1:
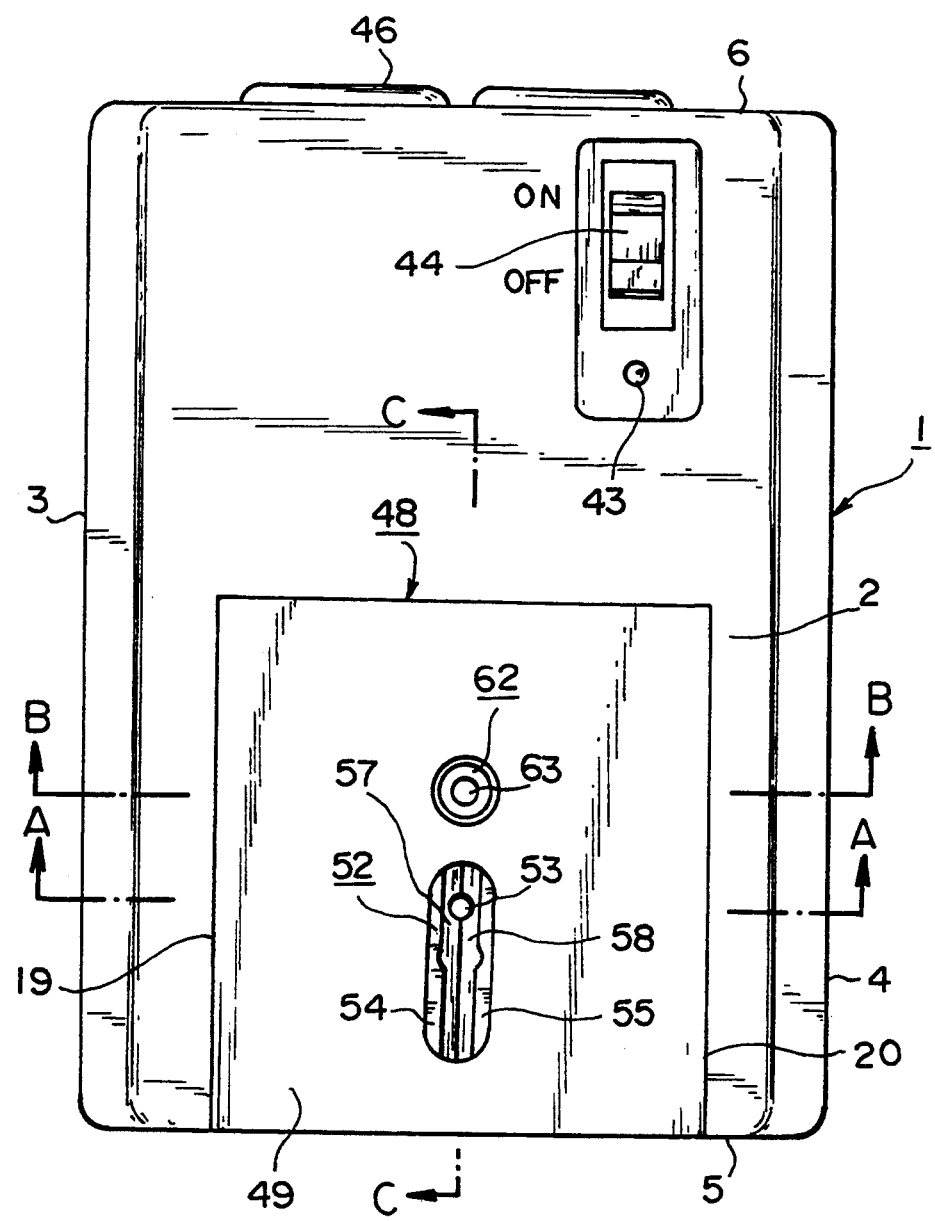
FIG. 1 is a plan view showing one example of the used injection syringe disposal apparatus according to the present invention.
Figure 2:
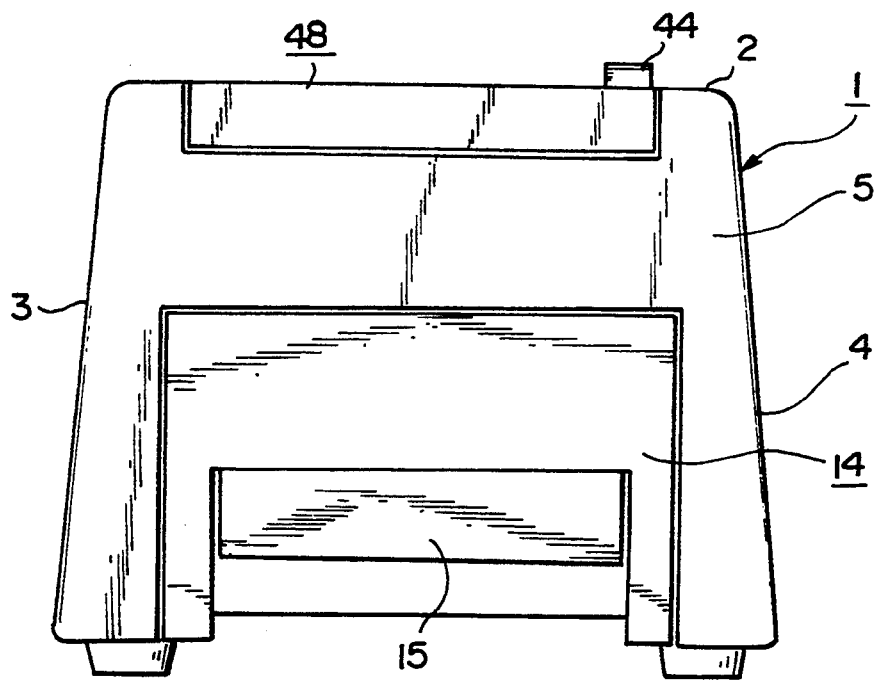
FIG. 2 is a front view depicting the used injection syringe disposal apparatus shown in FIG. 1.
Figure 3:
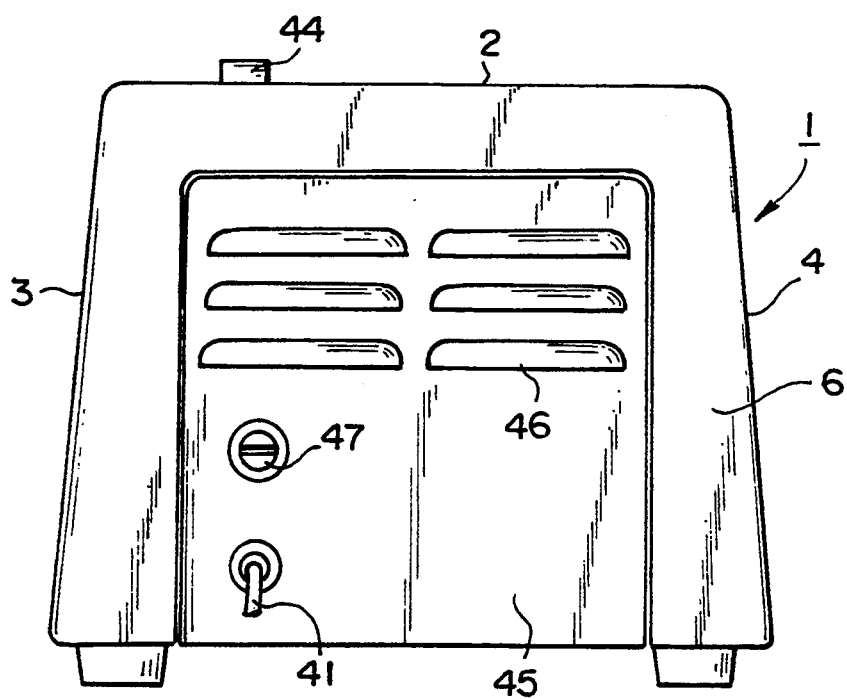
FIG. 3 is a rear view of the used injection syringe disposal apparatus above.
Figure 4:
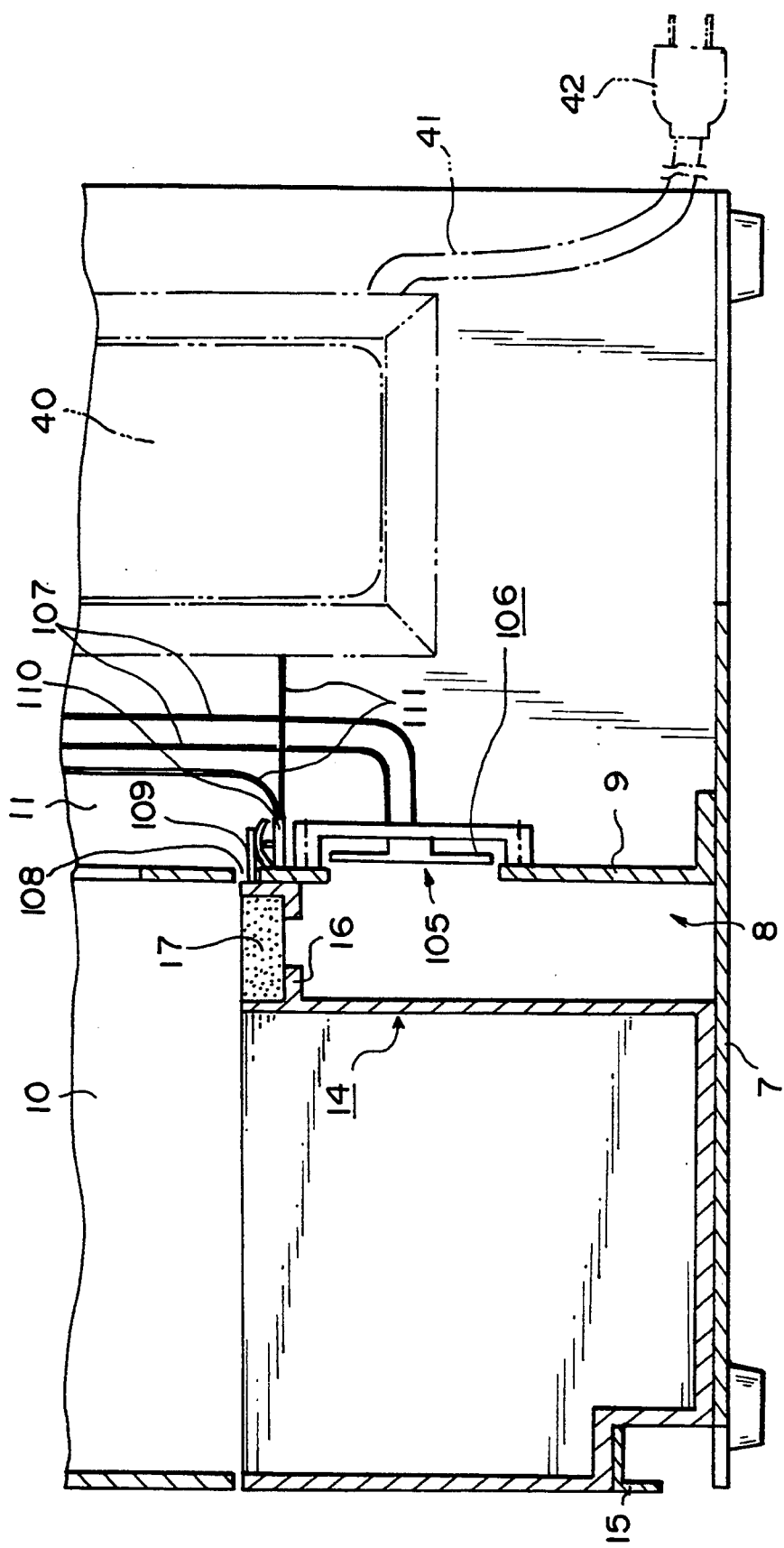
FIG. 4 is a partly-omitted enlarged sectional view depicting an important portion of interior of the housing of the disposal apparatus.
Figure 5:
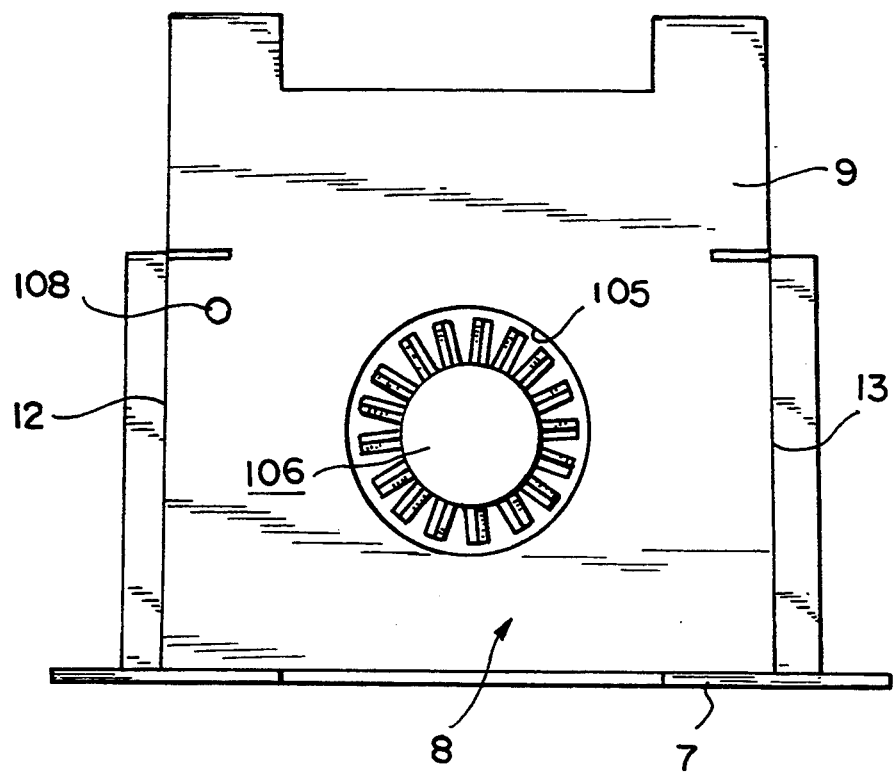
FIG. 5 is a front view depicting the fan arranged in the disposal apparatus.
Figure 6:
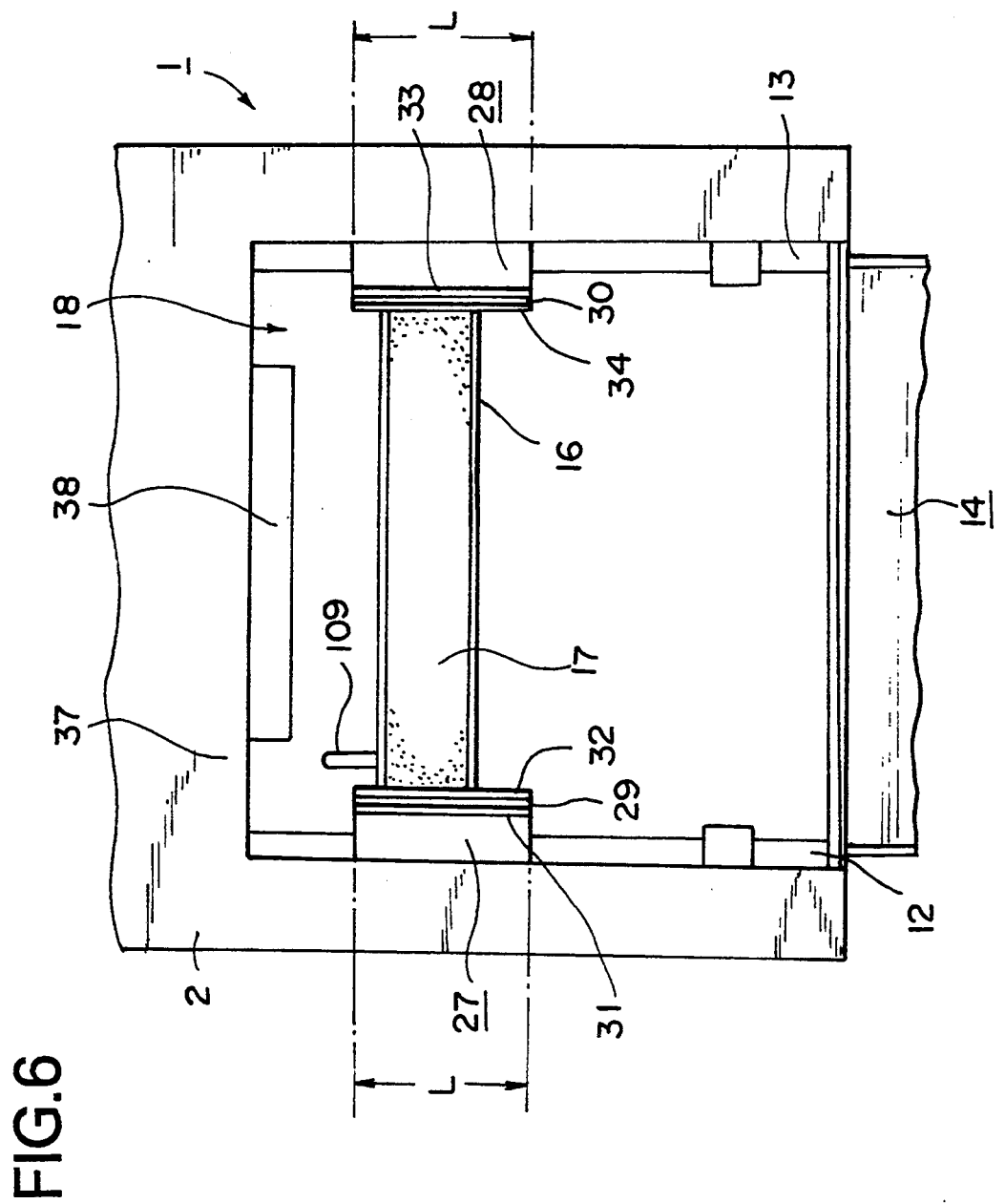
FIG. 6 is a partly-omitted enlarged sectional view depicting an important portion of interior of the housing after the cartridge type electrode plate unit is taken off.

FIG. 1 through FIG. 3 depict a preferable embodiment of the disposal apparatus for waste injection syringes of the present invention. As shown in these drawings, the disposal apparatus has a housing 1 and a cartridge type electrode plate unit. The housing 1 has a sectional shape of about letter ⊐ in Japanese and a ceiling wall 2, left and right side walls 3 and 4, a front wall 5, and a rear wall 6. The housing 1 is preferably made of right metal such as aluminum. As shown in FIG. 4 through FIG. 6, there is a base board 7 in interior of the housing 1. The interior is divided into two section 10 and 11 by a rear side erected wall 9 restricting a containing space 8 for scrap box. The containing space 8 is placed in one section 10 and formed the rear side erected wall 9 and left and right side walls 12 and 13. A scrap box 14 is placed in the scrap box containing space 8 so as to be drawn in and out of the space 8.

The scrap box 14 is made preferably of right metal such as aluminum and the like, and has a top opening and a handle 15 fixed on its front side. A deodrizer filling portion 16 integrally extending to the outside is formed on a top end of the rear side. The deodrizer filling portion 16 has an open top portion and urethane foam or nonwoven fabric is filled in the portion 16. Water soluble deodrizer 17 of mixture of ferrous sulfate and organic acid is soaked in the urethane foam or nonwoven fabric.

Figure 8:
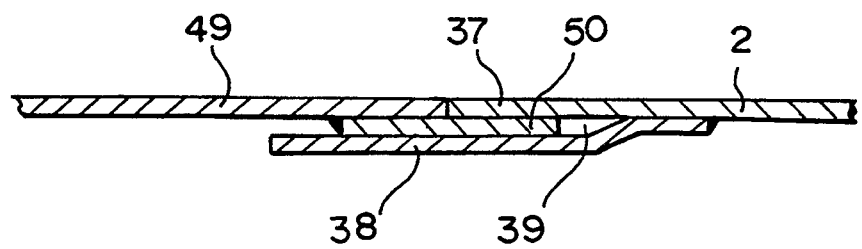
FIG. 8 is a partly-enlarged sectional view depicting installation condition of electrode plate unit on cut-off portion of ceiling wall of the housing.
Figure 9:
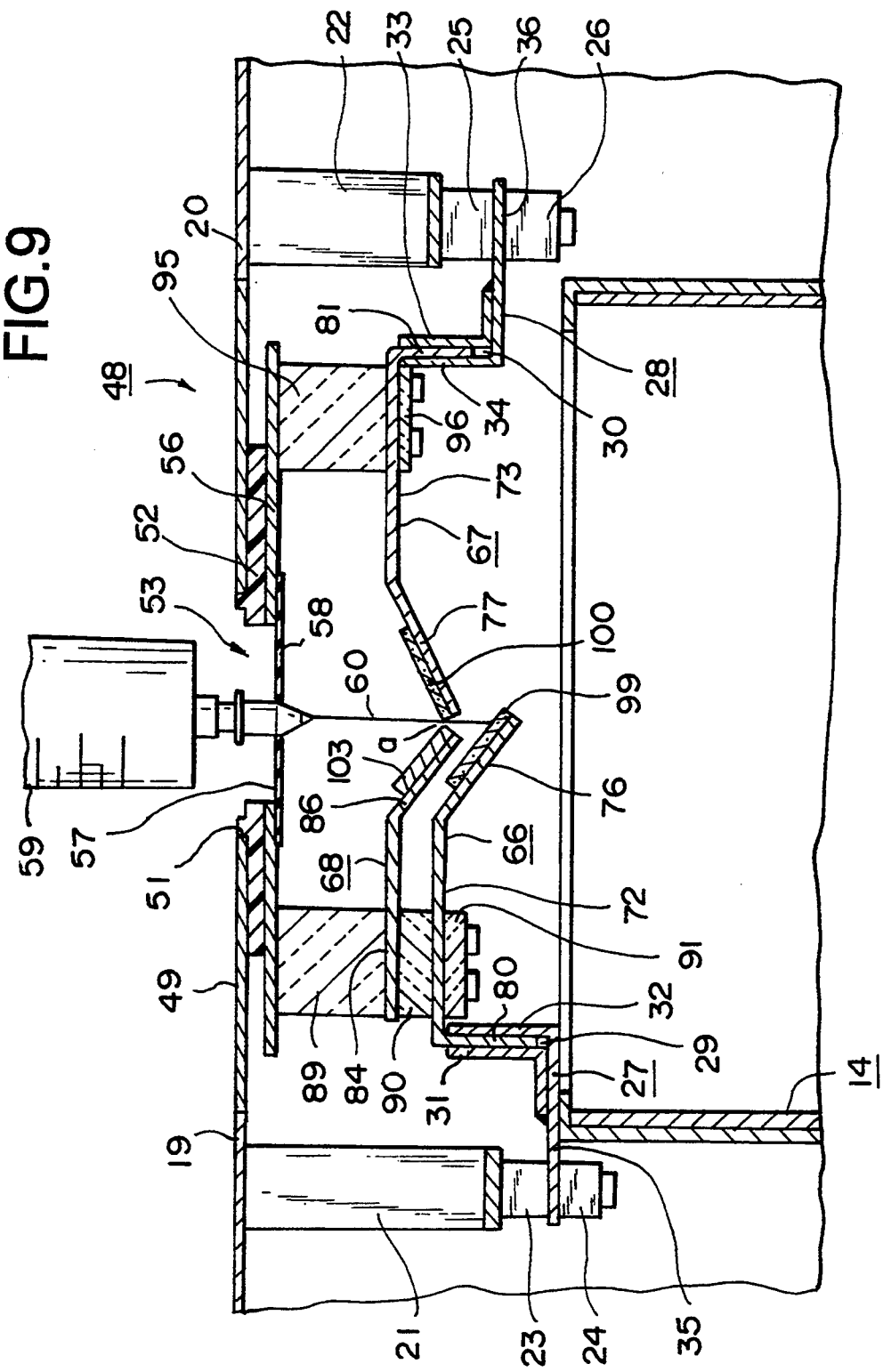
FIG. 9 is a partly-enlarged sectional view taken along line A—A shown in FIG. 1.

As shown in FIG. 6 and 9, a ⊐ shape cut-off portion 18 is formed in the ceiling portion facing the section 10 of the housing 1. Electrode plate contact terminals 27 and 28 are fixed electrically insulatedly to the ceiling wall 2. These electrode plate contact terminals 27 and 28 are placed below the left and the right edge portions 19 and 20 facing to each other and in the cut-off portion 18 and situated at positions near the closed side of the cut-off portion. These electrode plate contact terminals 27 and 28 are electrically insulated by fixing plates 21 and 22 pending from bottom faces of the ceiling wall 2 and welded thereto, and insulators 23, 24, 25 and 26. In detail, the electrode plate contacting terminals 27 and 28 has a sectional shape of about L letter and double perpendicular contact portions 31 and 32, 33 and 34, respectively having insertion gap portion 29 and 30 of springly sandwich structure, and horizontal portions 35 and 36. These horizontal portions 35 and 36 are placed between insulators 23 and 24, 25 and 26 respectively pending from the lower ends of the attaching plates 21 and 22 and attached there in electrical insulating condition (see FIG. 9 and 10). In addition, the contact terminal 28 is placed at a position higher than other contact terminal 27. As shown in FIG. 6 and 8, a leaf spring engagement member 38 has a front end portion protruding generally to an opening side and welded on the bottom face of the closed side edge portion 37 of ⊐ shape cut-off portion 18 of the housing 1 leaving a gap portion 39 between the front end portion and the closed side edge portion 37.

There is a power source transformer 40 in the section 11 of the housing 1 functioning to impress a secondary windings voltage to the electrode plate contact terminals 27 and 28. Also, the housing 1 has a power source cord 41 and a plug 42 for impressing electricity to the primary windings of the power source transformer 40. There are a pilot lamp 43 and power source switch 44 on the ceiling wall 2 of the section 11 of the housing 1. The rear side wall 6 of the housing 1 has a ventilation plate 45 provided with a ventilation or exhaust hole 46 integrally formed in the wall and the ventilation plate 45 has a power source fuse 47.

Figure 7:
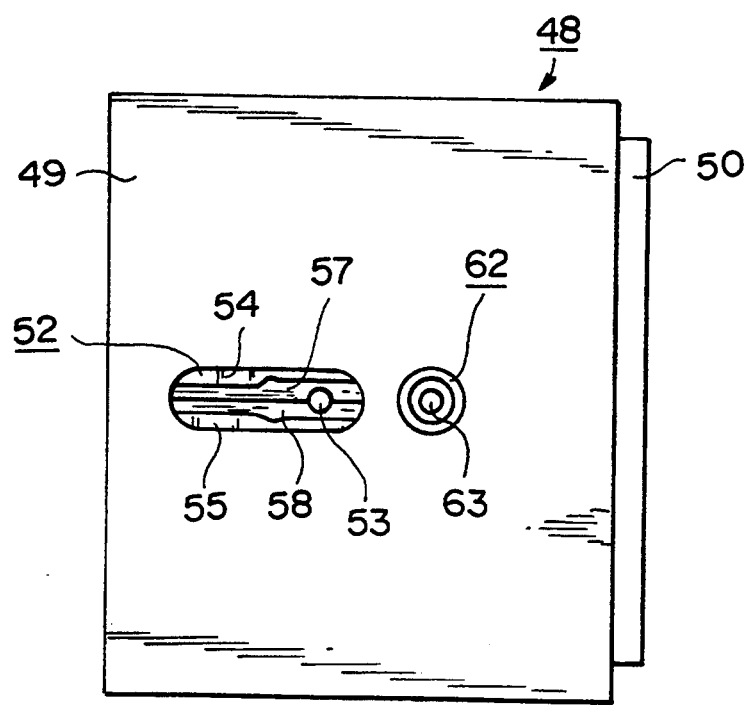
FIG. 7 is a plan view of the cartridge type electrode plate unit.

As shown in FIG. 1, the cartridge type electrode plate unit 48 is detachable to a ⊐ shape cut-off portion 18 of the housing 1. The cartridge type electrode plate unit 48 fits to or corresponds to, as shown in FIG. 7 and 8, a plane shape of the ⊐ shape cut-off portion 18, and has a square metal base plate 49 for wholly closing the cut-off portion 18. An insertion engagement portion 50 to be elastically inserted into the gap portion 39 between the edge portion 37 and the leaf spring engagement portion 38 is welded securely to the lower face of edge portion corresponding to the edge portion 37 of the ⊐ shape cut-off portion in the metal base plate 49. After the base plate 49 fits into the ⊐ shape cut-off portion c8, the base plate 49 becomes substantially on a level with the ceiling wall 2 of the housing 1.

An oval hole 51 is formed in the metal base plate 49 along its central longitudinal direction (drawing direction of the scrap box 14 ) from a point near front end edge to about the center point of the base plate 49. An injection syringe insertion hole 53 made of heat-resisting hard plastics and an injection syringe drawing-out guide member 52 having injection syringe drawing engagement protrusions 54 and 55, respectively formed on both the sides of the injection syringe insertion hole 53 are secured to the oval hole 51 by a fixing plate 56. Shield and blinder members 57 and 58 made of non-transparent, heat-resisting and elasticity, such as silicon rubber are secured to the lower face of the fixing plate 56 so as to face to each other. Consequently, the blinder members 57 and 58 shield or hide flash generated while thin injection syringes 60 of the injector 59 are melted and destroyed, as well as prevent odor generated while the destroying process from scattering or leaking out of the housing 1.

Additionally, an arc hole 61 is formed at a position a little near the front end along the same direction as that of the guide member 52 of the base plate 49. An injection syringe insertion guide member 62 made of good heat-resisting hard plastics and having a round stepped insertion hole 63 is secured to the lower face of the arc hole 61 in order to destory and melt thick screw-type injection syringe 65 of the thick injector 64.

Figure 10:
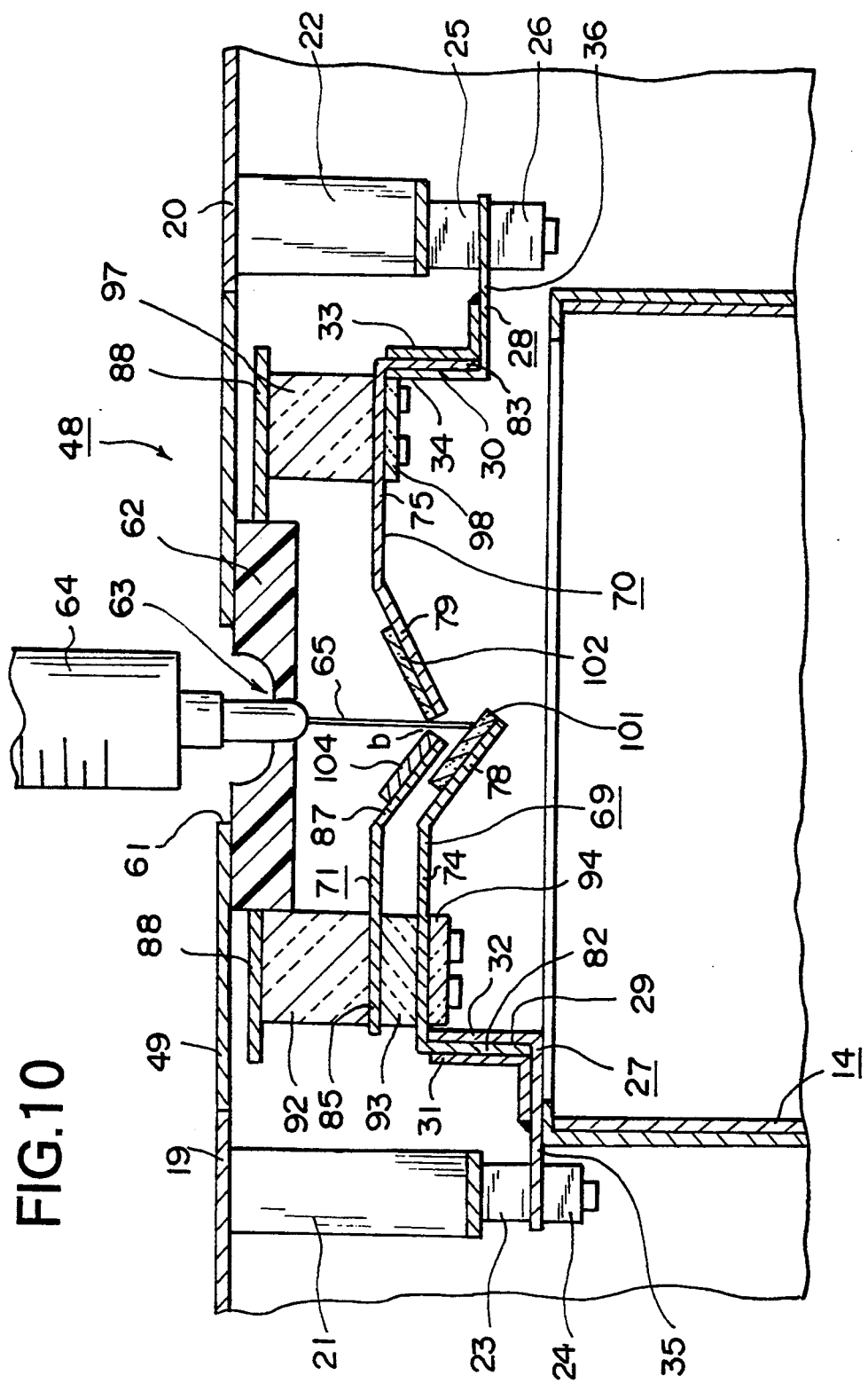
FIG. 10 is a partly-enlarged sectional view taken along line B—B shown in FIG. 1.
Figure 11:
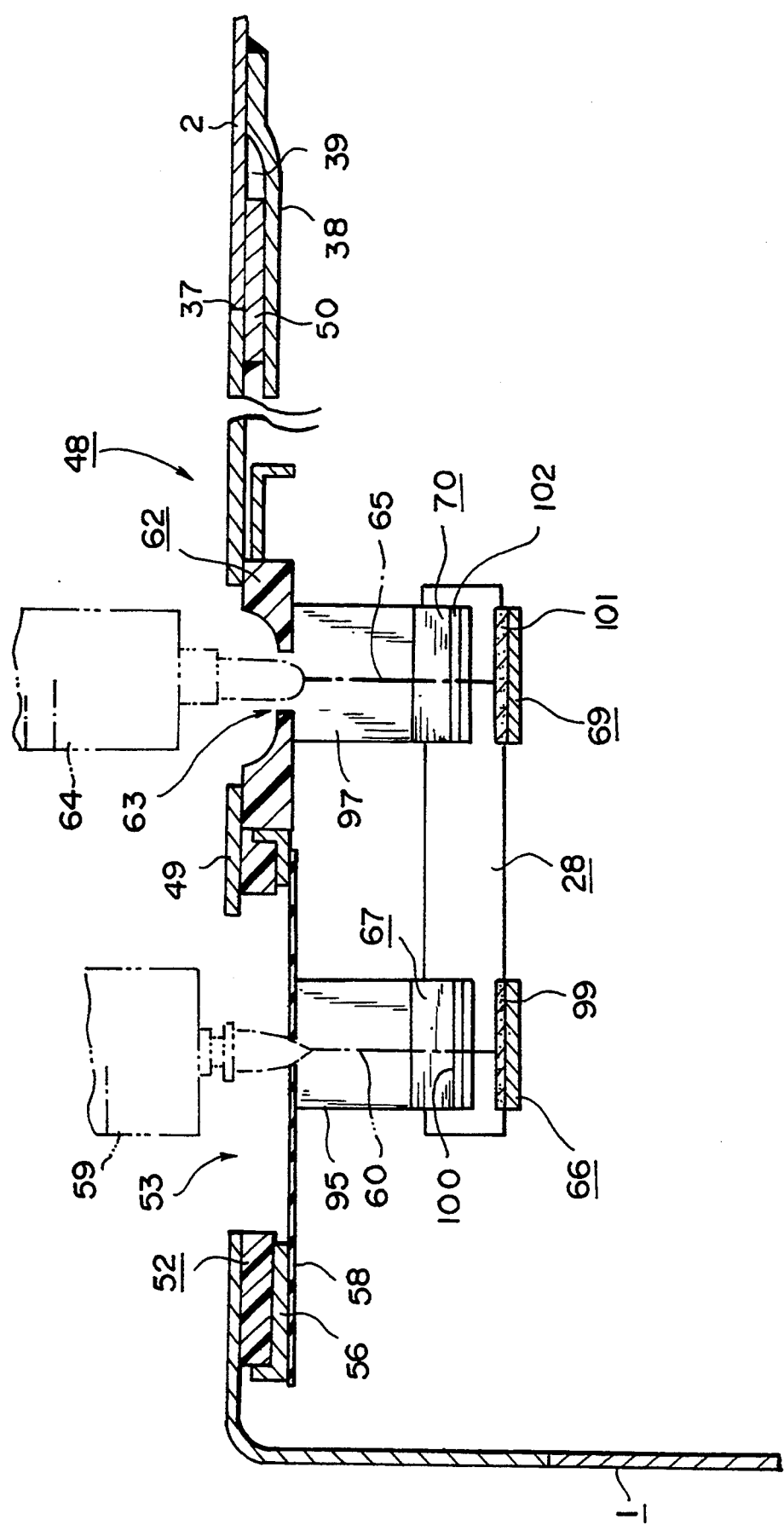
FIG. 11 is a partly-enlarged sectional view taken along line C—C shown in FIG. 1.

As shown in FIG. 9 to 11, a pair of electrode plates 66 and 67, a guide electrode plate 68 or a pair of electrode plates 69 and 70, and a guide electrode plate 71, respectively cross to each other and are separated and these plates are arranged on the lower face of the base plate 49. The thin injection syringe 60 of the injector 59 or thick screwed-in type injection syringe 65 of the injector 64, respectively inserted downwardly through the injection syringe insertion hole 53 or stepped insertion hole 63, come contact with these plates.

In more detail, respective pairs of electrode plates 66 and 67, 69 and 70 integrally have sequare and horizontal belt-like fixing portions 72, 73, 74, 75 made of good conductive electrical material such as phosphor bronze and the like, widely and square electrode fixing portions 76, 77, 78, 79 formed by bending front end portions of these square and horizontal belt-like fixing portions a little downwardly or slantly, and insertion terminal portions 80, 81, 82, 83 formed by bending rear end portions of these square and horizontal belt-like fixing protions a little downwardly and about at a right angle. Furthermore, the guide electrode plates 68 and 71 integrally have square electrode fixing portions 86 and 87, respectively formed by bending slightly downward and slantly. Ohter electrode plates 66 and 69, together with guide electrode plates 68 and 71 respectively arranged above the electrode plates 66 and 69, are secured through screws to insulators 89, 90, 91, 92, 93, 94 pending from fixing plates 56 and 88 by means of fixing portions 72, 74, 78, 85 of the electrode plates 66 and 69. These electrode plates 66 and 69 are electrically insulatedly secured to the base plate 49. Still other electrode plates 67 and 70 are electrically insulated and secured to the base plate 49. These electrode plates 67 and 70 have fixing portions 73 and 75 screwed to insulators 95, 96, 97, 98 pending from the fixing plates 56 and 88.

As shown in FIG. 9 and 10, respective pairs of carbon made electrodes 99, 100, 101, 102 formed in shape of square chip are secured or bonded to the upper faces of the electrode fixing portions 76, 77, 78, 79 of the pairs of electrode plates 66 and 67, and of electrode plates 69 and 70 through sandwiching using both side bending portions of respective fixing portions or soldering or other means. Metal made guide electrodes 103 and 104 are secured on the upper faces of the electrode fixing portions 86 and 87 of the guide electrode plates 68 and 71 through securing means identical with that of the electrode 99.

Furthermore, the guide electrode 103 and 104 guide the injector 60 or 65 when it vertically is inserted through the insertion hole 53 or stepped insertion hole 63. Accordingly, two points of the end and near the end of the injector 60 or 65 suitably come contact with the pair of electrodes 99 and 100 or 101 and 102. As shown clearly in FIG. 9, a distance of the gap (a) between the guide electrode 103 and carbon-made electrode 100 is determined to one through which an insertion type thin (diameter: 0.3 mm to 0.85 mm) injector 60 can be smoothly vertically inserted after being guided. And a distance of the gap (b) between the guide electrode 104 and the carbon-made electrode 102 is determined to one through which a screw-in type thick (diameter: 1.8 mm to 2.1 mm) injector 65 can be smoothly guided and vertically inserted. Respective pairs of carbon-made electrodes 99, 100, 101, 102 are made of high quality isotrophical carbon mainly consisting of fine carbon material, so that these electrodes have good characteristics of high conductivity, heat-resisting, wear-resisting and non-stickness repelling molten injector.

Respective pairs of electrode plates 66, 67, 69, 70 are adapted to have as shown in FIG. 9 and 10 insertion terminal portions 80, 81, 82, 83 which are adapted to elastically inserted between the gap portions 29 and 30 of the electrode plate contacting terminals 27 and 28 and contact electrically with each other when the electrode plate unit 48 fits as a cartridge into the shape cut-off portion of the housing 1.

As shown in FIG. 4 and 5, a circular opening 105 is formed in a position a little below the rear face erected wall 9 (a little below the deodrant filling portion 16 of the scrap box 14) forming a scrap box containing portion 8 in the housing 1. A small fan 106 is placed in an erected wall rear side surrounding the circular opening portion 105. Electric wire 107 connects the fan 106 with the secondary winding of the power source transformer 40. Operation of the fan 106 sucks odor gas generated while melting treatment of the injector syringe 60 (or injector 65) through the deodrant agent 17 and the odor gas is compulsorily exhausted out of the housing 1 through an air exit 46 of the room 11. As shown in FIG. 4 to FIG. 6 and FIG. 12, a switch rod 109 protrudes from the rear face side of the deodrant agent filling portion 16 of the scrap box 14. The switch rod 109 is adapted to slide through a through hole 108 of a rear face erected wall 9 in accordance with the sliding motion of the scrap box 14. A limit switch 110 is placed on a rear face side of the rear face erected wall 9 and is connected to the primary winding of the power source transformer 40 through lead wire 111. A sliding motion or out-and-in movement of the scrap box 14 makes the primary winding of the power source transformer 40 connected to respective pairs of electrode plates 66, 67, 69, 70 and the fan 106 turned on or off. During the time from the instant the scrap box 14 is drawn on this side and the scrap is taken-out to the instant the scrap box 14 is set in its original position, electricity is halted to impress to the electrode plates 66, 67, 69, 70 and the fan 106 in order to obtain safety and economy of power consumption of the destroy apparatus.

Figure 12:
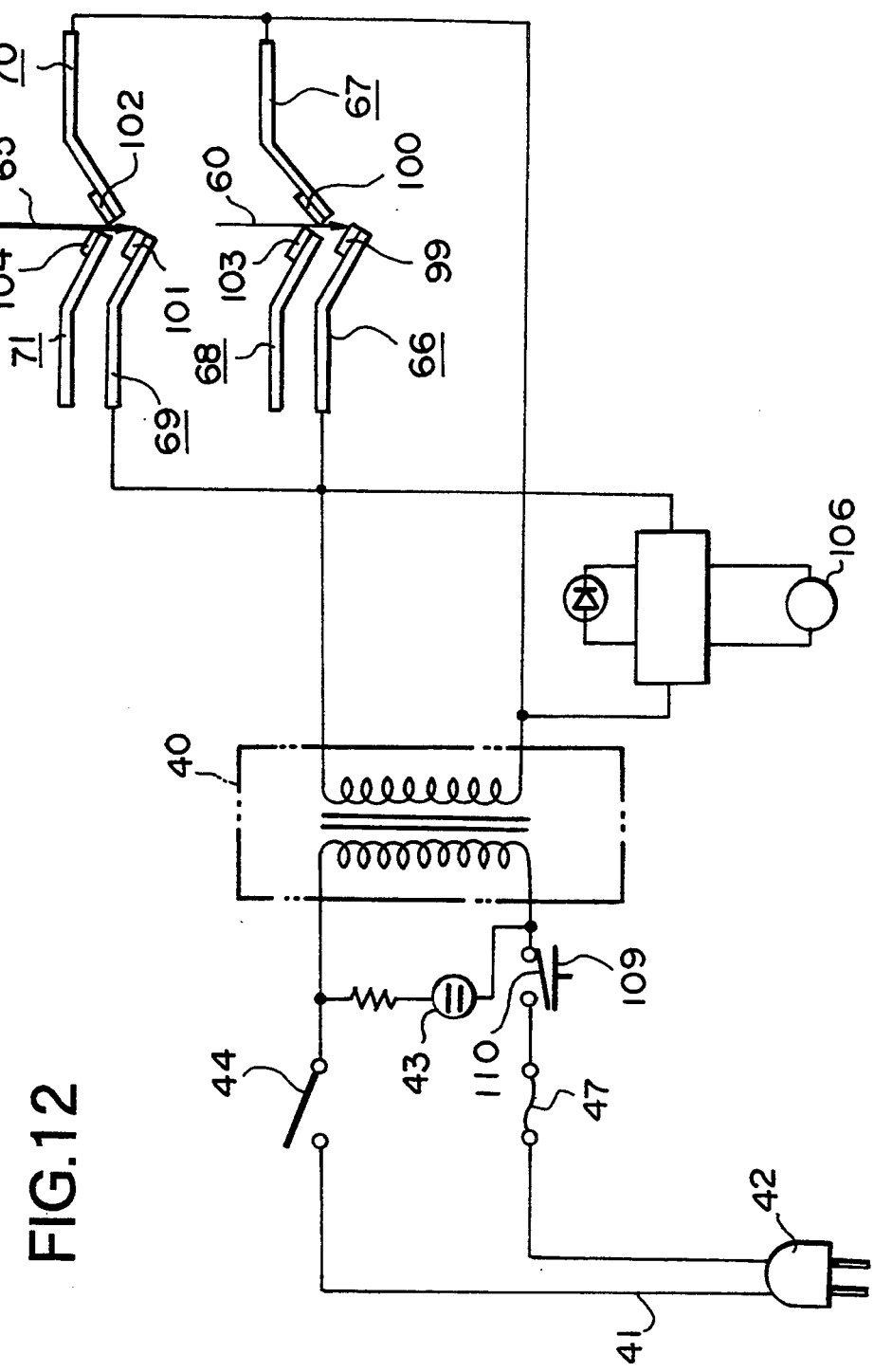
FIG. 12 is a whole structure of electric circuit of the disposal apparatus for waste injection syringes.

The power source transformer 40, cord 41, plug 42, pilot lamp 43, power source switch 44, fuse 47, electrode plates 66, 67, 69, 70, and fan 106 are electrically connected as shown in FIG. 12.

Next, usage method and function of the injector syringe destroy apparatus having the structure above will be explained.

When the plug 42 is put in a power source receptacle (not shown) and the power source switch 44 is turned on, the pilot lamp 43 is lit to demonstrate live-condition of electricity. When you want to destroy the thin (diameter: 0.3 mm to 0.85 mm) syringe 60 to be inserted into the injector 59, the syringe 60 inserted into the injector 59 lowers and is inserted through the insertion hole 53 of injection syringe drawing-out or pulling-out guide member 52. Then, the syringe 60 is guide so as to vertically inserted into the gap portion (a) between the guide electrode 103 and carbon-made electrode 100. When a front end or tip of the injection syringe 60 comes into contact with the lower carbon-made electrode 99 and simultaneously a portion of the syringe 60 a little above its tip comes contact with the upper carbon-made electrode 100 forming an electric circuit. As a result, much short-circuit electricity is impressed instantly to the injection syringe 60 and it will melt and destroyed.

When melting proceeds from the tip of the injection syringe 60 and reaches its base portion, the injector 59 is pulled upward through the insertion hole 53 and reaches pulling-out engagement protrusions 54, and 55, then drawn upward out of the insertion hole 53. Accordingly, the injection syringe 60 is displaced or left from the injector 59 by means of the pulling-out engagement protrusions 54 and 55. Because that the electrodes 99 and 100 are made of carbon, molten scraps of the used injection syringe 60 fail to attach to the electrodes 99 and 100 and falls down into the scrap box 14. Odor gas generated when the injection syringe 60 is molten passes through the deodrant agent 17 due to sucking operation of the fan 106 and compulsorily exhausted out of the housing 1 from the air exit 46. Consequently, odor gas is kept being exhausted not only while the syringe melting operation, but also when the scrap box 14 is pulled out of the housing 1, so that it is possible to use the syringe destroying apparatus of the present invention sanitarily and safely without any unpleasant feeling of odor of the operator.

The case that the thick (diameter: 1.8 mm to 2.1 mm) injection syringe 65 to be screwed in the injector 64 is melted and destroyed will be described.

When the syringe 65 screwed in the injector 64 lowers and inserted through the stepped insertion hole 63 of the syringe insertion guide member 62, the syringe 65 is guided by the guide electrode 104 and inserted vertically into the gap portion (b) between the guide electrode 104 and carbon-made electrode 102. When the tip of the syringe 65 strikes the lower carbon-made electrode 101 and simultaneously the portion of the syringe 65 a little above the tip contacts with the upper carbon-made electrode 102 obtaining an electric circuit, thus much short-current is flown instantly melting and destroying the injection syringe 65. Molten syringe 65 doesn't attach to the carbon-made electrodes 101 and 102 and the scraps of the molten syringe 65 fall down in the scrap box 14 and scraps are kept in the box while the fan 106 functions.

In addition, while the syringe 60 or 65 is in its melting operation, the inserted terminal portions 80 and 81 of the electrode plates 66 and 67 (or inserted terminal portions 82 and 83 of the electrode plates 69 and 70) are heated due to contact resistance. Because the lengthes of the electrode plate contact terminals 27 and 28 are sufficient, so that respective pairs of insertion terminal portions 80, 82, 81, 83 are serially contacted, contact resistance heat dissipates after passing through one electrode plate terminal portion which not belong to or included in the circuit. In other words, contact resistance heat is sucked into the non-heated electrode contact terminal portion preventing the electrode plate contact terminal from over-heating.

The operation above is repeated and molten syringe scraps are deposited and filled in the scrap box 14, then a handle 15 of the scrap box 14 is gripped and pulled out of the housing 1 and waste syringe scraps are disposed. When the scrap box 14 is pulled-out, the switch rod 109 keeping the limit switch 110 at its on condition moves along a pulling-out direction through the hole 108 making the limit switch 110 turned off. As a result, the primary winding of the power source transformer 40 is made open stopping power supply to the electrode plate contact terminals 27 and 28 and the fan 106. When the scrap box 14 is again pulled in the housing 1 as shown in FIG. 4, the switch rod 109 operates the limit switch 110 making the circuit impressed.

When the electrodes and similar parts are damaged or injured by mechanical and electrical shocks happened during long usage period of the used injection syringe destroying apparatus introducing failures in conductivity, and it is necessary to exchange the old electrode and similar parts with a new electrode plate unit of the same structure provided with new electrodes and to displace the electrode plate unit owing to necessity of cleaning and inspection of the electrodes and the similar parts, the electrode plate unit 48 at its condition shown in FIG. 1 is pushed back to this side, the insertion engagement member 50 elastically engaged by the leaf spring engagement member 38 is pulled out of the place. Accordingly, when the electrode plate unit 48 is pulled up or raised, the insertion terminal portions 80, 81, 82, 83 of the electrode plate 66, 67, 69, 70 are pulled out of the gap portions 29 and 30 of the electrode plate contact terminals 27 and 28 and the electrode unit 48 is displaced. Then, a new electrode plate unit 48 replaced with the old one or the old electrode plate unit 48 cleaned and checked is installed on the housing 1 of the syringe destroyer or disposal apparatus of the present invention by pushing the insertion engagement member 50 into the gap portion 39 left between the edge portion 37 of the shape cut-off portion 18 and the leaf spring engagement member 38, thus the electrode unit 48 is elastically or resiliently inserted and held. The base plate 49 is made about even with the housing ceiling wall 2 and they are seen as an integral portion and they are surely installed. Simultaneously, electrode plate insertion terminal portions 80, 81, 82, 83 of respective pairs of electrode plates 66, 67, 69, 70 are resiliently inserted into the insertion gap portions 29 and 30 of the electrode plate contact terminals 27 and 28 obtaining a sure and electrical connection between them. It is apparent that the electrode plate unit 48 can be surely installed on the housing 1 completely without troublesome operation of wiring and wire connection.

What is claimed is:

1. A used injection syringe disposal apparatus comprising a power source transformer installed in the apparatus, a housing provided with a ceiling wall, said ceiling wall having a cut-off portion through which a scrap box can slide, and a cartridge electrode plate unit adapted to engage and disengage with said cut-off portion of the ceiling wall of the housing, wherein a pair of electrode plate contact terminals connected to a secondary winding of said power source transformer is placed below edge portions faced to each other of the cut-off portion of the ceiling wall of the housing through fixing plates pending from a botton face of the ceiling wall and insulators, the cartridge electrode plate unit includes a base plate fully closing the cut-off portion of the ceiling wall of the housing, said base plate has an injection syringe insertion hole through which a thin syringe is inserted and an injection syringe pulling-out guide member having a pair of injection syringe pulling-out protrusions, and an injection syringe insertion guide member having a stepped insertion hole through which a thick injection syringe is inserted, respective pairs of electrodes adapted to contact with a tip portion of the thin injection syringe or the thick injection syringe, respectively inserted downwardly and a portion of the syringe a little above the tip are placed on the bottom face of the base plate, respective pairs of electrode plates provided with their terminal portions adapted to electrically contact with said pair of electrode plate contact terminals are provided so as to cross to each other and be separated and electrically insulated from said base plate, and when an injection syringe is bridged between respective pairs of electrode and contacts with each other, short-circuit current between the electrodes melts the injection syringe, and wherein a switch rod adapted to project and be withdrawn through a hole formed in a rear face erected wall of the housing according to sliding motion or taking in and out motion of the scrap box is formed on a rear face side of the scrap box, and a switch for opening and closing a primary winding of said power source transformer connected to said pair of electrode plate contact terminals and said fan, said switch functions in accordance with the operation of said switch rod.

2. The used injection syringe disposal apparatus according to claim 1, wherein a leaf engagement member is protruded from a bottom face side of a closed side edge portion of the cut-off portion of the ceiling wall of the housing, an insertion engagement member is protruded from the base plate of said cartridge electrode plate unit, and when the cartridge type electrode plate unit is installed, the insertion engagement member is inserted into the gap portion between the leaf spring engagement member and the ceiling wall of the housing, so that the cartridge electrode plate unit can be integrally and firmly installed.

3. The used injection syringe disposal apparatus according to claim 1, wherein a deodrant agent filling portion is provided the outside of a top end of the rear face side of the scrap box in the housing, deodrant agent fills the filling portion, and a fan for compulsorily exhausting odor gap generated while injection syringe melting operation out of the housing through said deodrant agent, the fan is connected to the secondary winding of the power source transformer.

4. The used injection syringe disposal apparatus according to claim 1, wherein guide electrode plates provided with guide electrodes are provided above the lower electrode plates of said respective pairs of electrode plates leaving gap portions corresponding to the thickness of the injection syringes from the electrodes of the respective upper electrode plates.

5. The used injection syringe disposal apparatus according to claim 1, wherein the electrodes of respective pairs are made of high quality isotropic graphite of mainly fine black lead material.

6. The used injection syringe disposal apparatus according to claim 1, wherein said pair of electrode plate contact terminals have a length such that the insertion terminal portions of the respective electrode plate serially contact with each other.

* * * * *